(12) United States Patent
Hamilton et al.

(10) Patent No.: US 6,767,715 B2
(45) Date of Patent: Jul. 27, 2004

(54) NITROSO COMPOUNDS AND THEIR USE AS SPIN TRAPS

(75) Inventors: Lynne Hamilton, Antrim (GB); Paul Graham Winyard, London (GB)

(73) Assignee: Randox Laboratories Ltd., Antrim (GB)

( * ) Notice: Subject to any disclaimer, the term of this patent is extended or adjusted under 35 U.S.C. 154(b) by 251 days.

(21) Appl. No.: 10/011,300

(22) Filed: Dec. 11, 2001

(65) Prior Publication Data

US 2002/0086338 A1 Jul. 4, 2002

(30) Foreign Application Priority Data

Dec. 12, 2000 (GB) .............................................. 0030278
Oct. 15, 2001 (GB) .............................................. 0124714

(51) Int. Cl.[7] ...................... G01N 33/543; G01N 24/00; C07C 309/40
(52) U.S. Cl. ...................... 435/7.92; 436/116; 436/119; 436/127; 436/173; 562/58
(58) Field of Search .................. 435/7.92; 436/116, 436/119, 127, 173, 115; 562/58

(56) References Cited

FOREIGN PATENT DOCUMENTS

| WO | WO 92/18874 | 10/1992 |
|---|---|---|
| WO | WO 02 31495 A | 4/2002 |

OTHER PUBLICATIONS

Roselaar et al., "Detection of oxidants in uremic plasma by electron spin resonance spectroscopy", Kidney International, vol. 48, 1995, pp. 199–206.

Ozawa et al. "Spin–Trapping Of Sulfite Radical Anion, $SO_3^-$, By A Water–Soluble, Nitroso–Aromatic Spin–Trap", Biochemical and Biophysical Research Communication, vol. 142, No. 2, 1987, pp. 410–416.

Matsuo et al., "Highly Sensitive Hepatitis B Surface Antigen Detection By Measuring Stable Nitroxide Radical Formation With ESR Spectroscopy", Free Radical Biology & Medicine, vol. 25, No. 8. pp. 929–935, 1998.

Reist et al., "Sulphite enhances peroxynitrite–dependent $\alpha_1$–antiproteinase inactivation. A mechanism of lung injury by sulphur dioxide?", FEBS Letters, 423, 1998, pp. 231–234.

Reist et al., "Toxic Effects of Sulphite in Combination with Peroxynitrite on Neuronal Cells", Journal of Neurochemistry, vol. 71, No. 6, 1998, pp 2431–2438.

Orrell et al., "Monomer–Dimer Solution Equilibria of 2,4, 6–Trialkylnitrosobenzenes and 2,4,6–Trialkylnitrosobenzene/Nitrosobenzene Mixtures. A Study Using One–and Two–dimensional NMR Techniques", J. Chem. Soc. Perkin Trans., 1990, pp. 1297–1303.

Azoulay et al., "Aromatic C–Nitroso Compounds. Thermodynamics and Kinetics of the Equilibrium between 2,6–Dimethylnitrosobenzene and its trans–Dimer", J.C.S. Perkin II, pp. 256–259.

Janzen et al., "Two Decades of Spin Trapping", Advances in Free Radical Chemistry, vol. 1, pp. 253–295.

*Primary Examiner*—Mary E. Ceperley
(74) *Attorney, Agent, or Firm*—Oliff & Berridge, PLC

(57) ABSTRACT

A compound of the formula

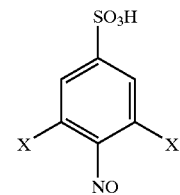

wherein X is Cl or $CH_3$, or a salt thereof, is useful as a spin trap in various assays.

10 Claims, 2 Drawing Sheets

NITROSO COMPOUNDS AND THEIR USE AS SPIN TRAPS

FIELD OF THE INVENTION

This invention relates to novel nitroso compounds and to their use as spin traps.

BACKGROUND OF THE INVENTION

It is now widely accepted that Reactive Oxygen (RO) and Reactive Nitrogen (RN) species (including free radicals) are involved in the pathogenesis of several disease states. The only technique which can detect low concentrations of radicals directly is electron spin resonance (ESR) spectroscopy. Although this technique is highly sensitive (thresholds of $10^{-7}$–$10^{-6}$M spins), it is not directly applicable to the study of biological oxidations. A more useful method, permitting ESR investigation of short-lived reactive free radicals by transforming them into more persistent species, is the so-called "spin trapping" method. The technique of spin trapping makes use of a diamagnetic compound in which all the electrons are in pairs. The diamagnetic compound, known as the spin trap, reacts with a free radical (R') which contains an unpaired electron with spin. Reaction of the spin trap with a reactive free radical, results in the formation of a relatively stable, ESR-observable spin adduct. In favourable cases, the free radical, R', can be identified from the ESR parameters of the spin adduct (e.g. hyperfine coupling constants, g-factor).

This technique was established by Jansen et al, JACS (1968) 90:5909–10. Since then, there has been much research on the synthesis of suitable spin traps. The spin traps that have been most commonly employed are those designed so that, on reaction with a free radical, a nitroxide is formed.

A commercially available spin trap is 3,5-dibromo-4-nitrosobenzenesulphonate, sodium salt (DBNBS). See Kaur et al, JCS Chem. Comm. (1981) 142–3. DBNBS is a water-soluble aromatic C-nitroso spin trap which has been reported to trap the sulphite radical anion ($SO_3^-$), superoxide, alkyl, nitric oxide and selenite anion radicals. DBNBS has also been reported to detect an oxidising species in uremic plasma, as it is oxidized to its radical cation DBNBS$^+$ which is then detected by ESR spectroscopy. See Roselaar et al, Kidney International (1995) 48:199–206, and WO-A-92/18874.

Reist et al, FEBS Lett. (1998) 423:231–4, indicates that sulphite is toxic to the lung and can cause allergic reactions such as bronchoconstriction in asthmatics. The toxic effects of sulphite in combination with peroxynitrite neuronal cells are reported by Reist et al, J. Nephrology (1998) 71:2431–8. An effective spin trap for sulphite is therefore of great potential value.

Matsuo et al, Free Radical Biology and Medicine (1998) 25:929–35, reports a very sensitive 'ELISA-ESR' method for Hepatitis B surface (HBs) antigen detection, using 4-hydrazonomethyl-1-hydroxy-2,2,5,5-tetramethyl-3-imidazoline-3-oxide (HHTIO) as the spin trap. In this method, beads are coated with the first HBs-antibody, and a second HBs-antibody is labelled with horseradish peroxidase (HRP). In the presence of HBs antigen, the HRP-labelled antibody will be linked to the antigen and the antigen linked to the beads. After washing, the antigen-antibody complex is added to a solution containing p-acetamidophenol (p-AP), hydrogen peroxide and HHTIO. The p-AP is converted into phenoxy radicals by the action of HRP in the presence of hydrogen peroxide, and the phenoxy radical is trapped by HHTIO to form a stable nitroxide radical which can be detected by ESR spectroscopy.

SUMMARY OF THE INVENTION

Novel compounds according to this invention are 3,5-dichloro-4-nitrosobenzenesulphonate (DCNBS) and 3,5-dimethyl-4-nitrosobenzenesulphonate (DMNBS) and salts thereof.

DCNBS at least has several advantages over DBNBS. These include improved solubility of the spin trap in aqueous systems and narrower ESR signals (which result in a greater signal/noise ratio).

DCNBS has been used successfully to detect an oxidant in the dialysate of patients with renal failure (the oxidant oxidized DCNBS to its radical cation DCNBS$^+$ which was subsequently detected by ESR spectroscopy).

DCNBS will trap nitric oxide. It is also a potential spin trap for alkyl free radicals, superoxide and the selenite radical anion ($SeO_3^-$).

DCNBS has been found to be a more sensitive spin trap than DBNBS for the sulphite radical anion ($SO_3^-$). DMNBS is also superior to DBNBS or its isotopic analogues ($^{15}$N and $d_2$), or DCNBS. DMNBS was shown to give an ESR signal for the $SO_3^-$ adduct of more than 20 times that obtained with DBNBS.

Accordingly, DMNBS as a spin trap for the sulphite radical anion has enormous potential. In addition, DMNBS may be used as a detector molecule for the presence of antibody-peroxidase complexes in ELISAs with ESR detection.

Description of the Preferred Embodiments

Preferred compounds of the invention are DCNBS sodium salt and DMNBS sodium salt. However, other salt forms are contemplated, and which retain the essential features of the invention.

DCNBS and DMNBS may be formulated and used in the same manner as DBNBS. DCNBS and DMNBS, and their respective salts, may be isotopically labelled using the isotope $^2$H or $^{15}$N. The synthesis and utility of DCNBS and DMNBS are described below.

For example, a compound of the invention may be used in assaying any suitable sample for the presence of sulphite radical anion, nitric oxide, alkyl free radicals or superoxide. A compound of the invention may also be used in an assay for an oxidant from the dialysate of a uremic patient. See also British Patent Application No. 0024938.3.

In an assay of the invention, radicals may be detected by ESR spectroscopy.

Figure 2:
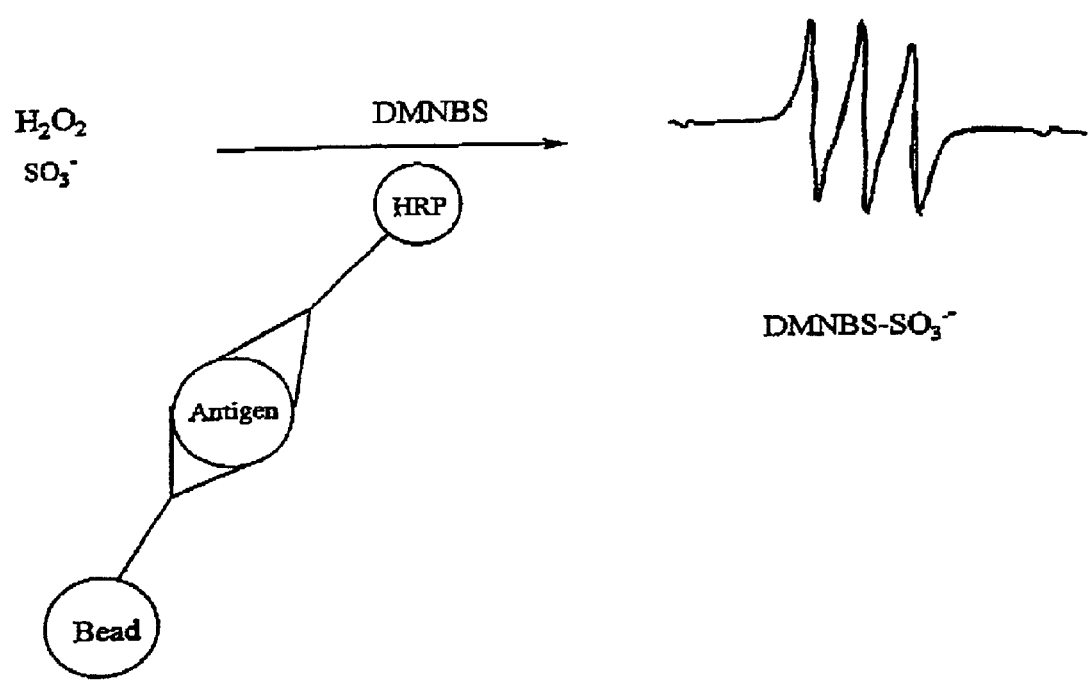
FIG. 2 is a schematic of a reaction generating DMNBS-$SO_3^-$.

In a particular embodiment of the invention, DMNBS may be used instead of HHTIO in the ELISA-ESR assay described above. Based on the same principles, the DMNBS-$SO_3^-$ adduct can be formed from a reaction mixture of sulphite, hydrogen peroxide and DMNBS by the action of HRP (FIG. 2). Many HRP-labelled antibodies are widely available. Preliminary results suggest that the DMNBS assay is superior to the HHTIO assay, indicating that a compound of the invention may be used as a detector molecule for the presence of antibody-peroxidase complexes in ELISAs with ESR detection.

The following Examples illustrate the preparation of compounds of the invention. The subsequent Tests illustrate their utility.

EXAMPLE 1

DCNBS was synthesised in two steps from 2,6-dichloroaniline (Aldrich Chemical Co.) as described below. For reference, DBNBS was synthesised from 3,5-dibromosulphanilic acid, sodium salt (Aldrich Chemical Co.) by the method of Kaur et al, supra. Horseradish peroxidase (Type VI), phosphate buffered saline tablets, hydrogen peroxide and dipotassium sulphite were all purchased from Sigma Chemical Company, Poole, Dorset, U.K.

3,5-Dichlorosulphanilic Acid.

2,6-Dichloroaniline (22.0 g; 0.136 mol) was added cautiously to concentrated sulphuric acid (50 ml) under nitrogen, with cooling and stirring. When addition was complete the reaction mixture was heated under nitrogen at 170° C. for 5 hr, then allowed to cool to 50° C. before pouring into cold water (4° C.). The precipitate was filtered and then heated with decolourising charcoal (2 g) in boiling water (500 ml) for 15 min. After filtration the solvent was removed and the crude product was recrystallised from water to give a crystalline solid, which was dried over silica gel overnight, to give 3,5-dichlorosulphanilic acid as a white powder. Yield 13.7 g (42%).

I.R. 1153 cm$^{-1}$ (s) ($SO_3^-$)

3,5-Dichloro-4-nitrosobenzenesulphonate, Sodium Salt (DCNBS)

3,5-Dichlorosulphanilic acid (2.0 g; 8.26 mmol) and 30% hydrogen peroxide (5.9 ml; 0.058 mol) were added to a solution of sodium acetate (0.68 g; 8.26 mmol) in glacial acetic acid (14 ml) and stirred until the solid was completely dissolved. The resulting solution was left to stand at room temperature for 14 days, after which time a portion of the solvent was removed on the rotary evaporator (water bath temperature 40–50° C.) until a solid product was just observed. The reaction mixture was then left to stand overnight at 4° C. The product was filtered and washed with glacial acetic acid (5 ml), absolute ethanol (10 ml), dioxane/diethyl ether (1:1) (10 ml) and absolute ethanol (10 ml). The product was dried over silica gel overnight, to give 3,5-dichloro-4-nitrosobenzenesulphonate, sodium salt as a cream powder. Yield 0.92 g (40%).

I.R. 1297 cm$^{-1}$ (s) (aromatic C-nitroso trans dimer)

FAB-MS (negative ion mode, using 3-NBA as the matrix).

Peaks observed at 254, 256, 258 a.m.u. (14%, 10%, 4%) which is consistent with M$^+$-Na for DCNBS.

EXAMPLE 2

3,5-Dimethylsulphanilic Acid

Freshly distilled 2,6-dimethylaniline (25 ml; 0.20 mol) was added cautiously to concentrated sulphuric acid (37.5 ml) with cooling and stirring. When addition was complete, the reaction mixture was heated at 170° C. for 5 hr, then allowed to cool to 70° C. before pouring into cold water (4° C.). The precipitate was filtered after standing for 15 min. It was then dissolved in 2M sodium hydroxide (600 ml) and heated with decolourising charcoal for 15 min. The mixture was filtered and allowed to cool. It was then acidified to pH 3 (with caution) using 2M hydrochloric acid. Upon cooling to 4° C., the product crystallised as a white solid. This was filtered and dried over silica gel under vacuum. Yield 18.4 g (45%).

I.R. 1155 cm$^{-1}$ (s) ($SO_3^-$).

M.S. (−E.I.) Peak observed at 200 (M$^+$-1.56%).

3,5-Dimethylsulphanilic Acid, Sodium Salt

Aqueous sodium hydroxide (2M) was added dropwise to a suspension of 3,5-dimethylsulphanilic acid (8.3 g; mmol) in water (50 ml) until all the acid had dissolved and the solution was just basic (pH 11). The solution was refluxed for 1 hr, the solvent was removed under reduced pressure to give a white solid which was dried over $P_2O_5$ under vacuum. Yield 8.0 g (87%).

I.R. 1167 cm$^{-1}$ (s) ($SO_3^-$). Literature states 1200–1145 cm$^{-1}$ ($SO_3^-$).

3,5-Dimethyl-4-nitrosobenzenesulphonate, Sodium Salt (DMNBS)

Anhydrous sodium acetate (3.09 g; 37.7 mmol) was dissolved in glacial acetic acid (84.6 ml) with stirring. To this solution was added 3,5-dimethylsulphanilic acid, sodium salt (8.39 g; 37.7 mmol) and hydrogen peroxide (30% w/v, 30.2 ml; 0.294 mol). The reaction mixture was heated at 60° C. for 1 hr and then stirred at room temperature for 2 hr. The reaction mixture was left to stand at room temperature overnight to give a crystalline product. The product was filtered and washed with glacial acetic acid (40 ml), ethanol (40 ml), dioxane/diethyl ether (1:1) (40 ml) and ethanol (40 ml) to give a pale yellow solid.

Yield 4.0 g (45%).

I.R. 1266 cm$^{-1}$ (s) (aromatic C-nitroso trans dimer).

FAB-MS (negative ion mode, using 3-NBA as the matrix). Peak observed at 214 (M$^+$-Na, 24%).

$^1$H nmr (400 MHz, $D_2O$) 2.42 (6H, s, 2×—C$\underline{H}_3$) and 7.68 (2H, s, 2-H and 6-H). $^{13}$C nmr (400 MHZ, $D_2O$) 18.2 (2×—CH$_3$), 126.8 (C-2 and C-6), 134.6 (C3 and C-5), 142.0 and 145.5 (C-1 and C-4).

Tests

ESR Analysis

ESR spectra were obtained using a prototype spectrometer (Jeol (U.K) Ltd., Welwyn Garden City, England) equipped with a TE$_{011}$ cylindrical cavity. Samples were analysed at room temperature in a WG-LC-11 quartz flat cell (Wilmad-Glass, Buena, N.J.). In general the instrument parameters were: microwave frequency 9.2 GHz, microwave power 4 mW, centre field (CF) 336.7 mT, sweep width (SW) ±5 mT, number of data points 4095, modulation frequency 100 kHz. For the spin traps reacted with horseradish peroxidase/$H_2O_2$/sulphite: sweep time 200 s, time constraint 0.1 s, modulation width 0.05. For the spin traps reacted with the oxidant and NO; sweep time 150 s, time constraint 0.3 s, modulation width 0.2 mT. A JEOL ES-DM1 digital manganese oxide marker (0.03 mm of the glass tube inserted per unit on the dial setting) with a dial setting of 500 was used to ensure the reproducibility between samples and to identify the position of the signals in the microwave field.

Reaction of $SO_3^-$(Horseradish Peroxidase/$H_2O_2$/Sulphite)

Solutions of the spin traps DBNBS, DCNBS and DMNBS (40 mM) (25, 50, 91, 75, 110.75, 125 and 156.25 µl for final concentrations of 4, 8, 14.68, 17.72, 20 and 25 mM in PBS) were added to 8 µl horseradish peroxidase (91 µM in PBS), 8 µl $K_2SO_3$ (100 mM in water) and 12.5 µl $H_2O_2$ (5 mM in PBS). The difference in the volume comprised PBS (pH 7.4). The final volume of the reaction mixture was 250 µl. The reaction mixture was mixed thoroughly and analysed by ESR spectroscopy after 25 min incubation at room temperature. Controls were run using individual reactants as well as the reaction mixture above in the absence of the spin traps.

The extent of formation of radicals by DBNBS and DCNBS was tested in the $SO_3^-$ system. When DBNBS was reacted with horseradish peroxidase/$H_2O_2$/sulphite, a triplet of doublets was observed under the ESR conditions specified above. The triplet was due to the nitrogen hyperfine splitting at position 4 of the benzene ring in the DBNBS molecule and the doublet was due to the hydrogen hyperfine splitting at the 2 and 6 positions of the benzene ring. When DBNBS is replaced by DCNBS, the large bromine atoms are replaced by the smaller chlorine atoms, which causes a reduction in the line width of the signal from 0.087 to 0.085 mT.

In this $SO_3^-$ system, DBNBS reached an optimal concentration at 17.72 mM and DCNBS at 20–25 mM. Therefore the sensitivities of the spin traps were compared at these concentrations. The respective signal/marker ratios were 3.33 and 10.62, indicating that DCNBS has 3 times greater sensitivity than DBNBS.

When the water-soluble spin traps DMNBS, DCNBS, DBNBS, DBNBS-$d_2$, DBNBS-$^{15}N$ and DBNBS-$d_2$-$^{15}N$ were compared as traps for the sulphite radical anion ($SO_3^-$) (generated from HRP, $H_2O_2$, $SO_3^{2-}$), DMNBS was found to give the largest ESR signal. The signal height was found to be more than twenty times that obtained for DBNBS. It was also found to be more than three times that obtained for the isotopically labelled DBNBS analogue DBNBS-$d_2$-$^{15}N$. Thus DMNBS is a particularly useful spin trap for the sulphite radical anion.

Reaction of Nitric Oxide

Figure 1:
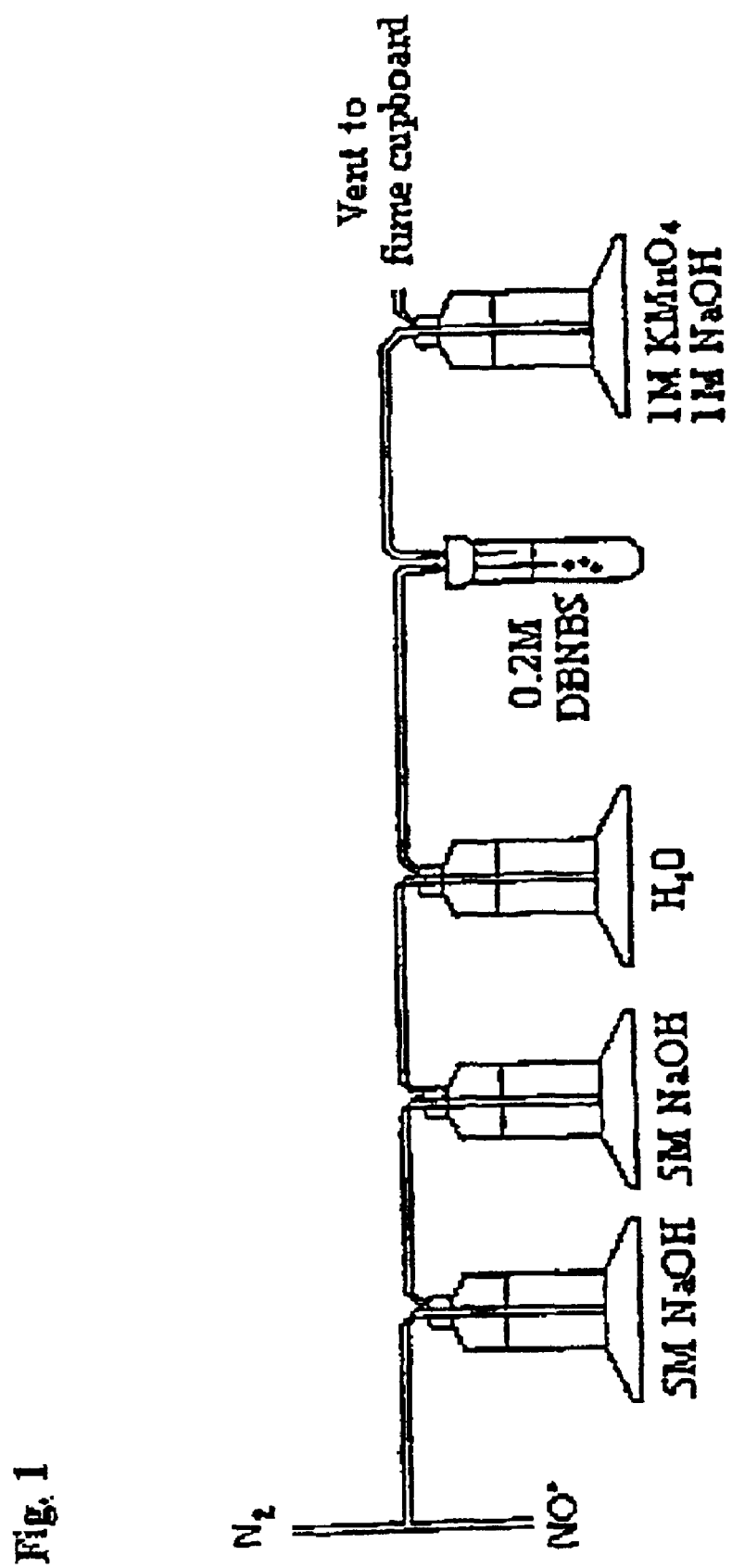
FIG. 1 is a schematic of an apparatus as used in the exemplified "Reaction of Nitric Oxide."

The apparatus shown in FIG. 1 was flushed with nitrogen for 15 min. The vacutainer containing deionised water (4 ml) was then connected to the system and flushed with nitrogen for a further 15 min, to remove any oxygen present in the system, and therefore to prevent the formation of nitrogen dioxide. The NO gas was bubbled through the deionised water via the system for 45 min. The small amount of nitrogen dioxide present in the pressurised NO container was removed by bubbling through two bottles of 5M NaOH. The gas was then bubbled through a scrubbing bottle containing deionised water to remove any alkaline aerosol contamination. Any excess of NO after the deionised water step was bubbled through a scrubbing bottle containing 1M potassium permanganate/1M NaOH to prevent excess NO escaping from the fume hood. The concentration of NO in the resulting NO-saturated water was taken to be 2.0 mM.

Spin Trapping Solutions

Samples of DBNBS, DCNBS and DMNBS were weighed into vacutainers and evacuated. Tris-HCl buffer, 0.01M, pH 7.4, was deoxygenated by bubbling with nitrogen gas for 15 min. The deoxygenated buffer was added to the spin traps by a gas tight syringe to give a final spin trap concentration of 0.30M. The spin trap solution was briefly flushed with nitrogen and was then ready for use.

Time Course

NO-saturated water (1 ml) was added to 1 ml of each of the spin trap solutions (DBNBS, DCNBS and DMNBS). The final concentrations of the spin traps were 0.15M and NO 1 mM. Parallel blanks were carried out by adding 1 ml of deoxygenated water to the spin trap solutions. At each time point samples were taken from test solutions and blanks for ESR spectroscopic analysis and the blank was substracted from the spectra.

The time course experiment showed that DBNBS (0.15M) reacted with NO (1.0 mM) very slowly under the conditions used. The reaction of DBNBS with NO was found to reach a maximum at approximately 50 hr. The reaction of DMNBS with NO was found to reach a maximum at 24–28 hr. The reaction of DCNBS with NO was found to proceed fastest, with a maximum being reached between 20–24 hr.

Dose Response of Spin Traps

The spin trap solutions were prepared as above to give final concentrations of 0.05, 0.1, 0.15, 0.2 and 0.25M in the reaction mixtures and the parallel blanks. The saturated NO solution (0.5 ml, final concentration 1 mM) was added to the test solutions and the deoxygenated water (0.5 ml) was added to the blanks. The reaction mixtures with DBNBS were incubated for 26 hr. while those with DCNBS were incubated for 22 hr. before analysis by ESR spectroscopy. The blanks were subtracted from their parallel test spectra respectively.

Sensitivity Study

The maximum signal intensity for DBNBS reacting with NO was obtained at a concentration of 0.15M DBNBS. For DCNBS reacting with NO, a plateau is observed from 0.05–0.40M DCNBS. Thus the concentration at which to assess the sensitivity of DBNBS and DCNBS reacting with NO was chosen as 0.15M.

The concentration of NO in NO saturated water is taken to be 2.0 mM. This NO solution was diluted with deoxygenated water to give final concentrations in the reaction mixture of 0, 0.25, 0.5, 1, 2.5, 5, 10, 50 and 100 $\mu$M. The NO solution was added to DBNBS and to DCNBS to give a final spin trap concentration of 0.15M. The blank (or zero point) was ran by adding 0.5 ml of deoxygenated deionised water to the spin trap solutions. The reaction mixture containing DBNBS was incubated for 50 hr, and that containing DCNBS was incubated for 20 hr. The signal to noise ratio was calculated from each spectrum. All withdrawals and additions of solutions were carried out using a gas-tight syringe.

The limit of detection (S/N ratio equals 3) and limit of quantitation (S/N ratio equals 10) were calculated from the linear part of the curve from 0 to 10 $\mu$M. The limit of detection and limit of quantitation for DCNBS were found to be 4.06 $\mu$M and 17.30 $\mu$M respectively. The limit of detection for DBNBS was found to be 0.23 $\mu$M and the limit of quantitation was 0.92 $\mu$M. Hence DBNBS was found to be a more sensitive spin trap than DCNBS for nitric oxide while DCNBS was found to react more quickly with NO than DBNBS.

Reaction of Oxidant

Dialysate from a patient with renal failure on Continuous Ambulatory Peritoneal Dialysis (CAPD) was used for this study. The dialysate was collected when the dialysate bag was changed.

Solutions of 10 mM DBNBS and DCNBS (5, 8, 12, 25 and 30 $\mu$l for final concentrations of 0.5, 0.8, 1.2, 2.5 and 3.0 mM) were added to 60 $\mu$l of the dialysate. The difference in volume comprised PBS. The reaction mixture was mixed thoroughly and analysed by ESR spectroscopy after 25 min incubation at room temperature.

When DBNBS and DCNBS were reacted with the oxidant, a typical three-line ESR signal was obtained. A reduction in peak width from 0.495 to 0.306 mT was observed when DBNBS was replaced by DCNBS. A reduction in peak width in ESR spectroscopy is generally regarded as beneficial, as it may lead to increased sensitivity.

To compare the sensitivity of DBNBS and DCNBS, the spin trap should be used in excess. Dose-response experiments showed that in the oxidant system DBNBS reached an excess at a final nominal concentration of ca. 1.2 mM, while DCNBS reached an excess at a final nominal concentration of 2.5 mM. Therefore the sensitivities of DBNBS and DCNBS were compared at 1.2 mM and 2.5 mM respectively. They were found to give almost identical results, viz respective signal/marker ratios of 0.516 and 0.521. DCNBS has the advantage that it is more soluble than DBNBS and consequently no turbidity problems have been encountered with DCNBS. Thus DCNBS is the preferred spin trap for analysis of the oxidant from the dialysate of uremic patients.

What is claimed is:

1. A compound of the formula

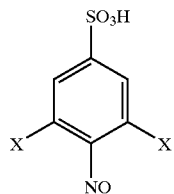

wherein X is Cl or $CH_3$, or a salt thereof.

2. 3,5-Dichloro-4-nitrosobenzenesulphonate or a salt thereof.

3. A compound according to claim 2, which is 3,5-dichloro-4-nitrosobenzenesulphonate, sodium salt.

4. 3,5-Dimethyl-4-nitrosobenzenesulphonate or a salt thereof.

5. A compound according to claim 1, which is isotopically labelled.

6. A compound according to claim 5, wherein the isotope is $^2H$ or $^{15}N$.

7. A method for detecting the presence of free radicals in a sample, comprising reacting a spin trap with a sample and detecting the formation of oxidized free radicals within the sample, wherein the spin trap comprises the compound of claim 1.

8. The method of claim 7, wherein the oxidized free radicals are sulphite radical anions, nitric oxide, alkyl free radicals, superoxide, oxidized versions of 3,5-dichloro-4-nitrosobenzenesulphonate, or oxidized versions of 3,5-dimethyl-4-nitrosobenzenesulphonate.

9. The method of claim 7, wherein the oxidized free radicals are detected by electron spin resonance spectroscopy.

10. The method of claim 7, wherein the oxidized free radicals are detected by the presence of an antibody-peroxidase complex in an enzyme-linked immunosorbent assay.

* * * * *